June 10, 1952 H. C. SWIM Plant Pat. 1,103
ROSE PLANT
Filed May 21, 1951
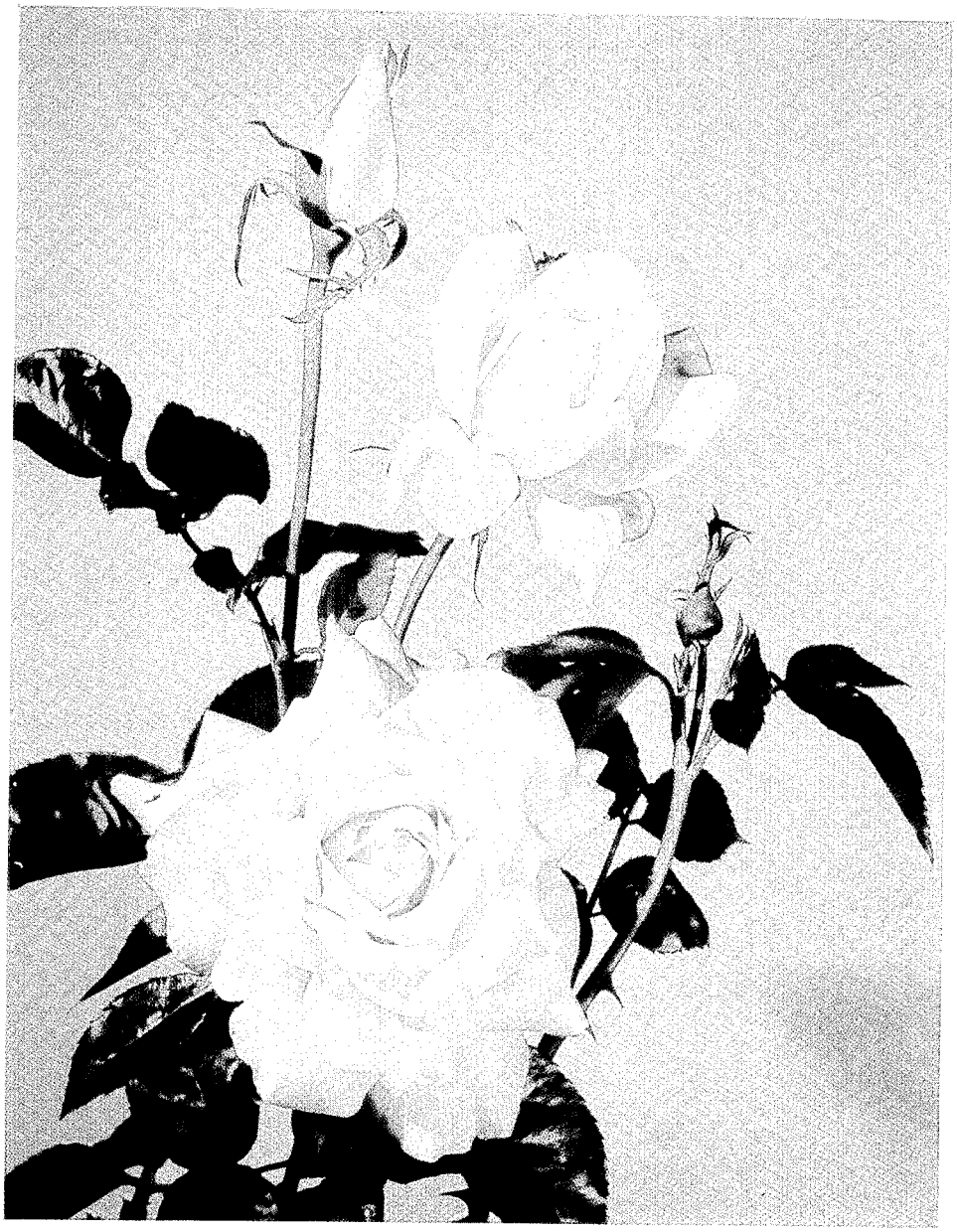
Inventor.
H. C. Swim
By: Robb & Robb
Attorneys Patented June 10, 1952

Plant Pat. 1,103

UNITED STATES PATENT OFFICE 1,103

ROSE PLANT

Herbert C. Swim, Ontario, Calif., assignor to Armstrong Nurseries, Inc., Ontario, Calif., a corporation of California Application May 21, 1951, Serial No. 227,286

1 Claim. (Cl. 47—61)

The present invention relates to a new and distinct variety of rose plant of the hybrid tea class, originated by me by crossing the well-known and popular variety "Charlotte Armstrong" (Plant Patent No. 455) with the variety "Contrast" (unpatented).

The new variety is principally characterized as to novelty by the following unique combination of characteristics which make it definitely distinct from its parents, as well as from all other varieties of roses heretofore known in commerce:

(1) The long-pointed to urn-shaped buds of multi-colored shades that are unusual and different from any known variety;

(2) The long-lasting quality of the buds when cut from the plant, this quality being substantially better than usually prevails in the average garden variety of rose of the hybrid tea class;

(3) The formal open flowers, resulting from the regular placement of the petals in an imbricated fashion;

(4) The attractive coloring of the buds and open flowers, as more particularly described in the following detailed description;

(5) The medium to large foliage of glossy appearance and moderate abundance.

In comparison with its seed parent "Charlotte Armstrong," the new variety has mature foliage that is more flat in form, more glossy in appearance and somewhat more abundant in quantity than the foliage of "Charlotte Armstrong." The multi-color coloring of the buds and open flowers of the new variety is quite distinctly different from the Spectrum Red to Blood Red color of the buds and open flowers of "Charlotte Armstrong," and in addition, the new variety has few small thorns, while "Charlotte Armstrong" is characterized by having many small thorns.

In comparison with its pollen parent "Contrast," the petal tips of the flowers of the new variety, and particularly the intermediate rows of petals, are distinctly pointed, whereas the petal tips of "Contrast" are characteristically rounded. While "Contrast" is a bi-color rose, the new variety is truly and popularly characterized as a multi-color rose. The open flowers of "Contrast" are more or less semi-double, with 15 to 25 petals, whereas the open flowers of the new variety are very double, with 60 to 70 petals. In addition, the mature foliage of "Contrast" is rolled downward at the margins, whereas the foliage of the new variety is relatively flat when mature.

Asexual reproduction of the new variety by budding at Ontario, California, shows that the foregoing characteristics and distinctions come true to form and are established and transmitted through succeeding propagations.

The accompanying drawing shows specimens of the new variety, with the flowers and foliage in different stages of development.

The following is a detailed description of the new variety, with color terminology in accordance with Robert F. Wilson's Horticultural Colour Chart, except where Ridgway's Color Standards and Nomenclature are noted in lieu thereof, or where ordinary dictionary terminology is obvious:

Type: Tall; bush; seedling; for cut flowers and for garden decoration.

Class: Hybrid tea.

Breeding: Seedling.

*Seed parent.*—"Charlotte Armstrong" (Plant Patent No. 455).

*Pollen parent.*—"Contrast" (unpatented).

Propagation: Holds its distinguishing characteristics through succeeding propagations by budding.

*Flower*

Locality where grown and observed: Ontario, California.

Flowers borne: Sometimes singly, usually two or more, to stem; in irregular cluster; on normal to strong, medium to long stems.

Quantity of bloom: Free to abundant; outdoors.

Continuity: Continuous during growing season.

Fragrance: Slight to moderate; tea.

Bud:

*Peduncle.*—Long; 8 to 12 cm.; average caliper to heavy; bending to erect; usually smooth; some gland-tipped cilia. Color—near Parrot Green, Plate VI (Ridgway); marked lightly with Deep Purplish Vinaceous, Plate XLIV (Ridgway), on the side exposed to the sun, also coloring the stipitate glands.

*Before calyx breaks.* — Size — medium. Form—medium length; pointed; ovoid; with foliaceous appendages; occasionally a few gland-tipped cilia on the surface of the bud; usually with slender, much cut foliaceous parts extending beyond the tip of the bud equal to ¾ or more of its length.

*As calyx breaks.* — Color — near Uranium Green, Plate 63/2, page 63, rapidly becoming near Rose Bengal, Plate 25, page 25; as the sepals spread, the color in this area which is first exposed becomes Rose Opal, Plate 022, page 110.

*Sepals.*—Inner surface—with tomentum; margins of sepals covered by adjacent sepals have tomentum; exposed margins have stipitate glands.

*As first petal opens.*—Size—average to large. Form—medium length; pointed; ovoid to somewhat urn-shaped. Color—outside: where first exposed by the spreading of the sepals in the darkest portions, it is near Chrysanthemum Crimson, Plate 824/3, page 169. Lighter portions of the petal which were more recently exposed by the parting of the sepals are Rose Opal, Plate 022/1, page 110. A small area near the base of the petal is near Citron Green, Plate 763/3, page 100; inside: near Straw Yellow, Plate 604/2, page 67, slightly washed with Rose Opal, Plate 022/3, page 110. The basal portion of the petal is near Canary Yellow, Plate 2/1, page 2.

*Opening.*—Opens up well; is not retarded from opening by cold, hot, wet or dry weather.

Bloom:

*Size.*—When fully open—average to large; 3½ inches to 4½ inches.

*Petalage.*—Very double (usually with no stamens showing); from 60 to 70 petals; plus 5 to 15 petaloids; arranged regularly.

*Form.*—Full; high centered at first and remaining high centered. The outside petals roll somewhat tightly outward. The intermediate petals are at first reflexed, becoming later at maturity loosely rolled outward. The inner petals are at first slightly cupped with the tips reflexed; later at maturity they are reflexed, with the innermost petals often twisted. The petal arrangement in the fully opened flower is imbricated, except for the outermost petals which are reflexed, and the center petals which are twisted. In over-all appearance the flower is formal.

Petals:

*Texture.*—Medium thick; with inside slightly velvety and outside satiny.

*Shape.*—Outside—nearly round; scalloped, usually with 1 to 3 notches. Intermediate—obovate. Inside—nearly oval to obovate, mucronate.

*Color.*—Colors may be modified by being marked, overlaid, shaded and/or washed with other colors.

This description of a newly opened flower was made from a rose grown outdoors in the month of September, at Ontario, California; hot weather 92° F. in daytime, 60° F. at night:

*Color.*—Outside petal—outside surface: near Fuchsine Pink, Plate 627/3, page 78, underlaid with Straw Yellow, Plate 604/2, page 67, especially in the basal half of the petal. The outer petals which were the first to unfold are occasionally near Tyrian Rose, Plate 24/2, page 24, with shadings as dark as Spiraea Red, Plate 025, page 112. Basal area is near Canary Yellow, Plate 2/2, page 2; inside surface: near Straw Yellow, Plate 604/2, page 67, blotched or overlaid with Rose Madder, Plate 23/2, page 23, especially in the upper portions of the petal but often overlaying nearly the entire surface. Basal area is near Canary Yellow, Plate 2/1, page 2. Intermediate petal—outside surface: near Empire Yellow, Plate 603/2, page 66, often washed near the petal tip with Camellia Rose, Plate 622/3, page 148; basal region near Canary Yellow, Plate 2/2, page 2; inside surface: near Naples Yellow, Plate 403/1, page 121, gradually changing to near Canary Yellow, Plate 2/1, page 2, in the basal region, washed near the petal tip with Carmine Rose, Plate 621/2, page 75. Inner petal—outside surface: between Empire Yellow, Plate 603/2, page 66, and Naples Yellow, Plate 403, page 121; inside surface: between Empire Yellow, Plate 603/2, page 66, and Naples Yellow, Plate 403, page 121.

This description was made from a rose that was open for three days outdoors in the month of October, at Ontario, California; temperature near 100° F.

*Color.*—Outside petal—outside surface: basal region is Barium Yellow, Plate 503/3, page 131, fading gradually upward to near white at upper margins; inside surface: basal region is near Canary Yellow, Plate 2/2, page 2; most of the petal is near white, washed lightly with near Camellia Rose, Plate 622/3, page 148, in area of upper petal margin. Inside petal—outside surface: near Canary Yellow, Plate 2/3, page 2, in basal region, fading rapidly upward so that most of the petal is near white; inside surface: basal area near Canary Yellow, Plate 2/2, page 2, fading rapidly upward so that the upper one-half of the petal is near white, washed lightly with near Camellia Rose, Plate 622/3, page 148, in the upper half of the petal.

*General color effect.*—Newly opened flower—center near Empire Yellow, Plate 603/2, page 66; outer portions of flower Rose Madder, Plate 23/2, page 23. Three days open—from near white to Camellia Rose, Plate 622/3, page 148.

*Behavior.*—Drop off cleanly; fading to near white; affected by hot weather by colors becoming less intense.

*Flower longevity.*—On bush in garden—4 to 5 days in October (95° F.). Cut roses grown outdoors kept at living-room temperatures—3 to 5 days in September.

*Reproductive organs*

Stamens: Average number, approximately 55 in number; arranged regularly; a few mixed with petaloids.

Filaments: Short to medium length; 6 to 9 mm. long; a few without anthers.

Anthers: Medium size; all open at once approximately. Color—central portions near Naples Yellow, Plate 403, page 121. Outer portions near Maize Yellow, Plate 607, page 69.

Pollen: Moderate. Color—near Maize Yellow, Plate 607, page 69.

Pistils: Average number to many, approximately 110 in number.

Styles: Moderately even; average length 10–12 mm. long, including ovary; thin to average caliper; loosely bunched; mixed with tufted silk-like white hairs.

Stigma: Color—near Naples Yellow, Plate 403, page 121. Style color at upper extremities near Pomegranate Purple, Plate XII (Ridgway).

Ovaries: Most protruding from calyx.

Hips: Average length, ¾ inch to 1⅛ inches; obovoid to globular; smooth; walls thick, fleshy. Sets few hips. Color—near Chalcedony Yellow, Plate XVII (Ridgway).

Sepals: Falling soon; medium length; spear-shaped; recurved. Color—inside—from fully opened flower: near Biscay Green, Plate XVII (Ridgway); at the base near Acajou Red, Plate XIII (Ridgway); in central portion these colors are modified by being overlaid with a heavy whitish tomentum; outside—from fully opened flower: near Biscay Green, Plate XVII (Ridgway).

Seeds: Average number, 10 to 20 in number; medium size.

Foliage:

*Leaves.*—Compound of usually 3 to 5 leaflets; normal to abundant; medium size; moderately heavy; semi-glossy.

*Leaflets.*—Shape—ovoid with apex acute; base round; margin doubly serrate.

*Color.*—Mature—upper surface: near Dark Dull Yellow-Green, Plate XXXII (Ridgway); under surface: near Light Grape Green, Plate XLI (Ridgway). Young—upper surface: near Absinthe Green, Plate XXXI (Ridgway), overlaid heavily at first with Livid Brown, Plate XXXIX (Ridgway); under surface: near Livid Brown, Plate XXXIX (Ridgway).

*Rachis.*—Average size. Upper side—grooved with stipitate glands on edges; under side—moderately smooth with prickles.

*Stipules.*—Medium length; medium width with short points, turning out at an angle of 45°, recurved toward the stem.

*Disease.*—Mildly subject to mildew.

Growth:

*Habit.*—Bushy; upright; moderately branched.

*Growth.*—Vigorous.

*Canes.*—Medium to heavy caliper.

*Main stems.*—Color—near Courge Green, Plate XVII (Ridgway). *Large prickles.*—Several; medium length; hooked slightly downward; with medium-length moderately narrow base. Color—near Hazel, Plate XIV (Ridgway). *Small prickles.*—Very few. Color—near Hazel, Plate XIV (Ridgway). *Hairs.*—None.

*Branches.*—Color—near Courge Green, Plate XVII (Ridgway). *Large prickles.*—Several; medium length; almost straight; hooked slightly downward; with medium length narrow base. Color—near Courge Green, Plate XVII (Ridgway), heavily overlaid with Cacao Brown, Plate XXVIII (Ridgway). *Small prickles.*—Few. Color—near Lime Green, Plate XXXI (Ridgway), overlaid near base with Dark Vinaceous, Plate XXVII (Ridgway). *Hairs.*—None.

*New shoots.*—Color—near Absinthe Green, Plate XXXI (Ridgway), overlaid with Dark Vinaceous, Plate XXVII (Ridgway). *Large prickles.*—None. *Small prickles.*—Few to several. Color—near Dark Vinaceous, Plate XXVII (Ridgway). *Hairs.*—None.

I claim:

A new and distinct variety of rose plant of the hybrid tea class, characterized as to novelty by its long-pointed to urn-shaped buds, by the multicolored coloring of its buds and open flowers, by the long-lasting quality of the buds when cut from the plant, by the formal open flowers resulting from the regular placement of the petals in an imbricated arrangement, by the very double form of the flowers and the pointed tips of the petals thereof, and by the abundance of its relatively flat, medium to large foliage of glossy appearance, substantially as herein shown and described.

HERBERT C. SWIM.

No references cited.